(12) United States Patent
Klein et al.

(10) Patent No.: US 11,879,725 B2
(45) Date of Patent: *Jan. 23, 2024

(54) OPTICAL MEASURING METHOD AND OPTICAL MEASURING DEVICE

(71) Applicant: DENTSPLY SIRONA INC., York, PA (US)

(72) Inventors: Konrad Klein, Heidelberg (DE); Peter Fritz, Mannheim (DE); Anders Adamson, Darmstadt (DE)

(73) Assignee: DENTSPLY SIRONA INC., York, PA (US)

( * ) Notice: Subject to any disclaimer, the term of this patent is extended or adjusted under 35 U.S.C. 154(b) by 326 days.

This patent is subject to a terminal disclaimer.

(21) Appl. No.: 17/258,836

(22) PCT Filed: Jun. 11, 2019

(86) PCT No.: PCT/EP2019/065147
§ 371 (c)(1),
(2) Date: Jan. 8, 2021

(87) PCT Pub. No.: WO2020/011464
PCT Pub. Date: Jan. 16, 2020

(65) Prior Publication Data
US 2021/0298884 A1  Sep. 30, 2021

(30) Foreign Application Priority Data

Jul. 10, 2018  (DE) .................. 102018211369.6

(51) Int. Cl.
*G01B 5/00* (2006.01)
*A61C 19/04* (2006.01)
(Continued)

(52) U.S. Cl.
CPC ........ *G01B 5/0014* (2013.01); *A61B 1/00009* (2013.01); *A61B 1/00194* (2022.02);
(Continued)

(58) Field of Classification Search
CPC ... A61B 1/00009; A61B 1/00036; A61B 1/24; A61B 5/0062; A61B 5/0088;
(Continued)

(56) References Cited

U.S. PATENT DOCUMENTS

2007/0150228 A1* 6/2007 Fukumoto .......... G01B 11/2518
                                                            702/155
2014/0272765 A1   9/2014 Andreiko
(Continued)

FOREIGN PATENT DOCUMENTS

EP        3090680 A1   11/2016
WO     2017062044 A1   4/2017

OTHER PUBLICATIONS

International Search Report; PCT/EP2019/065147; Aug. 26, 2019 (completed); dated Sep. 4, 2019.
(Continued)

*Primary Examiner* — Tri T Ton
(74) *Attorney, Agent, or Firm* — DENTSPLY SIRONA INC.

(57) ABSTRACT

The invention relates to an optical measuring method for three-dimensionally capturing the surface of an object by means of an optical capturing unit, wherein the optical capturing unit is moved relative to the object during a first measurement time period, the object is illuminated by the capturing unit with an illumination beam having a light intensity, height images are captured by the capturing unit in succession at a capturing frequency, at least some of the captured height images during the measurement time period are added to form a total height image and the total height (Continued)

image is displayed, and the light intensity and/or the capturing frequency are controlled during the measurement time period by control signals, the control signals being produced at time intervals during the measurement time period and each control signal being produced on the basis of at least one sensor signal of a temperature sensor.

10 Claims, 1 Drawing Sheet

(51) Int. Cl.
    *G01B 11/24*      (2006.01)
    *A61B 1/00*      (2006.01)
    *A61B 1/24*      (2006.01)

(52) U.S. Cl.
    CPC ............. *A61C 19/04* (2013.01); *G01B 11/24* (2013.01); *A61B 1/24* (2013.01); *G01B 2210/52* (2013.01)

(58) Field of Classification Search
    CPC . A61B 5/1077; A61B 5/4542; A61B 1/00194; A61C 19/04; A61C 9/0053; A61C 9/006; G01B 11/24; G01B 11/25; G01B 2210/52; G01B 5/0014; G06T 7/55; H04N 13/221

See application file for complete search history.

(56) References Cited

U.S. PATENT DOCUMENTS

| | | |
|---|---|---|
| 2018/0140394 A1 | 5/2018 | Atiya |
| 2021/0102892 A1* | 4/2021 | Oron ....................... G01S 17/36 |
| 2021/0267461 A1* | 9/2021 | Klein ....................... A61B 1/24 |

OTHER PUBLICATIONS

Written Opinion of the International Searching Authority; PCT/EP2019/065147; Aug. 26, 2019 (completed); dated Sep. 4, 2019.
International Preliminary Report on Patentability; PCT/EP2019/065147; Aug. 26, 2019 (completed); dated Sep. 4, 2019.

\* cited by examiner

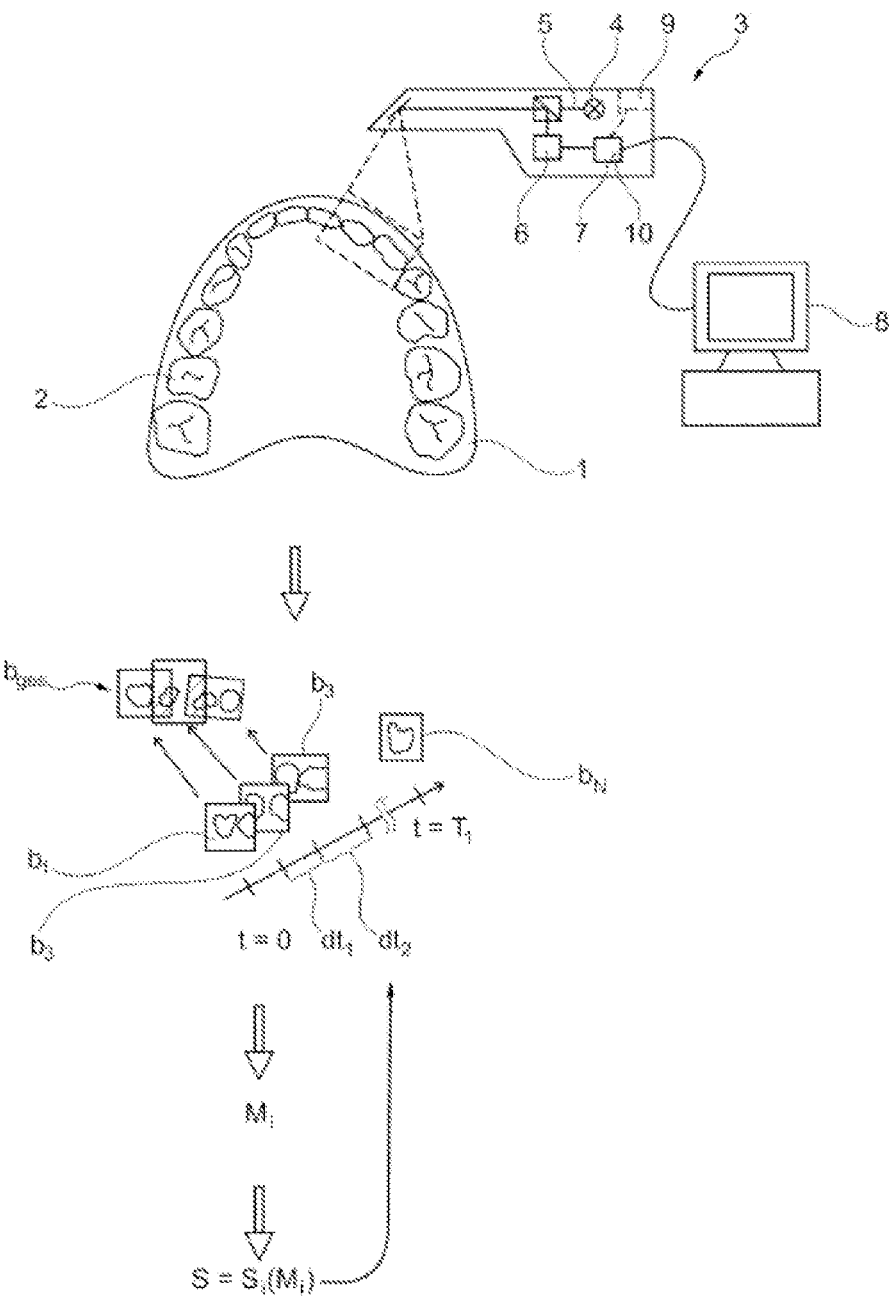

OPTICAL MEASURING METHOD AND OPTICAL MEASURING DEVICE

CROSS-REFERENCE TO RELATED APPLICATIONS

This is a National Phase application of International Application No. PCT/EP2019/065147, filed Jun. 11, 2019, which claims the benefit of and priority to German Application Ser. No. 102018211369.6, filed on Jul. 10, 2018, which are herein incorporated by reference for all purposes.

TECHNICAL FIELD

The invention relates to an optical measuring method for the three-dimensional detection of the surface of an object using an optical recording unit, wherein the optical recording unit is moved relative to the object during a first measurement time interval, the object is illuminated by the recording unit using an illumination beam with a light intensity, and height maps are successively detected by the recording unit at a recording frequency, wherein the detected height maps are already added to an overall height map during the measurement time interval and the overall height map is displayed.

BACKGROUND OF THE INVENTION

EP 2 172 799 A1 discloses an optical measuring apparatus that allows a three-dimensional optical detection of an object by means of a confocal imaging system. The optical measuring apparatus known from WO 2015/036467 also works confocally and additionally with a moving pattern projected onto the object.

In order to measure objects whose size exceeds the size of the recording region of the measuring apparatus, several individual images are generated and assembled into an overall image. The individual images are generated successively, while the measuring apparatus and the object are moved relative to one another. The relative orientations of the individual images relative to one another must be determined for the assembly of the individual images. This step is referred to as registration. Algorithms for registering image data are known, for example, from "A Method for Registration of 3-D Shapes" by Besl et al., IEEE Transactions on pattern analysis and machine intelligence, vol. 14, no. 2, 1992, or from "Multiview Registration of Large Data Sets" by Pulli, Proceedings, Second International Conference on 3D Digital Imaging and Modeling, Ottawa 1999, pp. 160-168.

Both the generation of projection patterns or of light for illuminating the object in general and the registration and transmission of the individual data sets requires energy, wherein the waste heat resulting from the energy consumption is undesirable in particular for measuring apparatuses to be used intraorally, e.g., intraoral cameras.

One way to reduce heat generation or avoid unnecessary heat generation is to avoid the generation of unnecessary image data sets, i.e., image data sets not required for the overall image.

In order to avoid unnecessary images, it is known, for example, to direct the user through feedback during the recording time interval. For example, DE 10 2014 207 667 A1 discloses displaying to the user already detected regions of the object in a standard model during the recording. The user can react accordingly and does not have to measure the already sufficiently measured regions again.

In light of this background, the object of the present application is to improve the known measuring apparatuses and measuring methods and in particular to reduce the energy consumption and computing effort in a reliable manner and, if possible, independently of the user.

SUMMARY OF THE INVENTION

The object is achieved by an optical measuring method according to Claim 1 and an optical measurement system according to Claim 10. Advantageous developments are listed in the dependent claims.

One subject matter of the invention is an optical measuring method for the three-dimensional detection of the surface of an object using an optical recording unit and an optical measurement system designed for carrying out the optical measuring method, with an optical recording unit, a computer-readable storage unit, a computing unit, and a display unit.

During a first measurement time interval, the optical recording unit is moved relative to the object, wherein the object is illuminated by the recording unit using an illumination beam with a light intensity and height maps are successively detected by the recording unit at a recording frequency. At least a portion of the detected height maps is added to an overall height map and displayed during the measurement time interval.

The light intensity and % or the recording frequency are regulated by means of control signals during the measurement time interval. The control signals are generated at intervals during the measurement time interval, wherein each control signal is generated on the basis of at least one sensor signal of at least one temperature sensor.

A further subject matter of the invention is an optical measurement system, comprising an optical recording unit, a computer-readable storage unit, a computing unit, and a display unit, wherein the optical measurement system is designed to carry out the optical measuring method described here.

Referred to as a height map is a pixel matrix or image matrix in which each pixel or image point contains three-dimensional information, namely the three-dimensional position of the object surface or the height of the object surface for the respective image point in the recording region. The three-dimensional information was extracted, for example, from an image sequence, e.g., by means of phase shift triangulation. The overall height map is composed of the many height maps recorded during the measurement time interval so that objects can also be measured whose size exceeds the size of the recording region of the recording unit.

A time span between switching on the optical recording unit and switching off the optical recording unit is referred to as first measurement time interval.

It goes without saying that the recording frequency and the light intensity can basically take on any values. Accordingly, the illumination can, for example, be temporarily switched off during the measurement time interval, i.e., the light intensity can be reduced to zero. During the measurement time interval, there may also be regular dead times during which the light intensity is zero.

The light intensity is regulated, for example, by means of the current or the duty cycle or the duty factor. i.e., the ratio of pulse duration to period duration.

One advantage of the method according to the invention and the apparatus according to the invention is reliable and simple control of the heat generation of the recording unit.

The control signal is advantageously generated additionally on the basis of at least one parameter of the recording unit and/or of at least one already detected height map.

If the recording frequency and the light intensity of the illumination are kept as low as possible, energy and/or computing effort can be saved and unnecessary heat generation can be avoided. On the other hand, a certain illumination intensity or recording frequency is necessary to detect a recording region and to obtain a certain quality. The transmission of recording data from the recording unit to a computing unit can also be temporarily suspended to save energy and limit heat generation.

By detecting a state of the measuring method during the measurement, it is possible to adapt the recording frequency and/or the light intensity to the current state in a timely manner and thereby ensure sufficient quality on the one hand and, on the other hand, the lowest possible energy consumption and/or computing effort.

The state of the measuring method is determined during the measurement time interval by means of one or more additional sensors or based on parameters of the recording unit or based on previously detected data or based on a combination of the aforementioned alternatives. The state can be any variable relevant to the measuring method or the overall image, e.g., a sampling density, a speed of the recording unit or a size of an overlap of consecutive images or a temperature of the optical recording unit. The recording frequency and/or illumination intensity is then adapted to the determined state.

It goes without saying that the most current values of the temperature sensor and of the additional sensor and/or of the recording unit and/or the last recorded height map are respectively used for each control signal in order to take into account the current state of the recording unit and/or of the recorded data as much as possible.

For generating the control signals, a computing unit is provided, for example, which communicates with the optical recording unit via a cable or wirelessly. Alternatively, a computing unit can be integrated in the optical recording unit.

The control signals are generated at fixed time intervals, i.e., at a fixed frequency. Alternatively, the control signals are generated at irregular time intervals, e.g., due to a trigger signal. According to another alternative embodiment, an at least temporally associated control signal is generated for each detected height map so that the time interval for the control signal generation is based on the recording frequency of the height maps.

The regulation of the recording frequency as a function of a current state of the image makes it possible to avoid the recording of unnecessary data on the one hand and, on the other hand, to ensure that sufficient data are still detected to generate an overall height map.

If the optical recording unit is located, for example, over regions not yet detected or over regions that have so far only been detected incompletely, the recording frequency is increased. On the other hand, the recording frequency is reduced if the optical recording unit is located over already completely or almost completely detected regions. The extent of the detection is determined, for example, based on the overlap of the last recorded height map with previously recorded height maps and/or from movement data and/or position data of the recording unit. Movement data and/or position data are determined, for example, from one or more detected height maps or one or more sensor signals of one or more corresponding sensors. Alternatively, a color image camera can also be used as a sensor according to the invention in addition to motion sensors and/or temperature sensors.

By regulating the light intensity, the latter is also adapted to the current state of the image during the measurement time interval. As a result, the light intensity can be reduced whenever possible, wherein sufficient quality of the data is ensured.

For example, the last detected height map or several already detected height maps or the previously generated overall height map are analyzed with regard to a surface condition of the object region contained therein. If the portion of the object currently located in the recording region has steep edges, for example, the light intensity is increased, while the light intensity is reduced in case of smoother topology.

The recording frequency and/or the light intensity can also be adapted to the state of the recording unit. For example, the recording frequency and/or the light intensity are reduced as soon as one or more parameters of the recording unit indicate undesired beating of the recording unit. The recording frequency can also be reduced, for example, if a data volume formed by the height maps and/or the overall height map exceeds a predeterminable or predetermined limit value or a computing unit generating the overall height map is overloaded.

One advantage is therefore reduced energy consumption, which in particular also reduces heating of the recording unit. At the same time, it is ensured that the quality of the images or the overall height map is not reduced.

Preferably, a statistic of an overlap of the last detected height map with a height map detected immediately before and/or a statistic of an overlap of the last detected height map with the overall height map is determined for generating each control signal for the respectively last detected height map, and a control signal corresponding to the statistic is generated.

Typically, for the registration of the respective new height map with the height maps already recorded, i.e., the determination of the alignment or orientation of the new height map relative to the already detected height maps, an overlap of the last detected height map with the height map detected immediately before or with the overall height map is determined. The overlap is also suitable as a measure for the amount of data already available for an object region and for determining a speed and/or movement direction of the optical recording unit relative to the object.

According to a development, the sensor signal of the at least one sensor is additionally taken into account when determining the overlap. It is in particular advantageous to combine an evaluation of the overlap, i.e., of the progress of the detection, with a temperature control, i.e., a sensor detecting the temperature of the optical recording unit or of the computing unit.

Alternatively or additionally, for generating each control signal for the respectively last detected height map, a surface increase of a total surface area contained in the overall height map is determined by means of a surface contained in the last detected height map and a control signal corresponding to the surface increase is generated. The surface increase is also suitable as a measure for the amount of data already available for an object region and for determining a speed and/or a movement direction of the optical recording unit.

The detected height maps or the overall height map assembled from the height maps can be represented in different ways. It is advantageous, for example, to identify or represent an object surface within the volume data set as a triangulated network. For example, the surface can be represented according to the method described in "Marching Cubes: A High Resolution 3D Surface Construction Algorithm," W. E. Lorensen and H. E. Cline, ACM SIGGRAPH Computer Graphics, vol. 21, no. 4. pp. 163-169, August 1987. Such a representation of the object surface allows a particularly simple and thus particularly energy-efficient determination of the surface increase.

A sampling density or a camera speed of the optical recording unit is advantageously determined from the statistic of the overlap or from the surface increase and is used for generating the control signal.

Alternatively or additionally, for generating each control signal for the respectively last detected height map, the overall intensity and/or the maximum intensity and/or the contrast and/or the number of extracted data points and/or a quality of extracted data points and/or the signal-to-noise ratio and/or the contrast of a color image additionally generated is determined and used to generate the control signal. All pixels or image points detected by the recording unit and used for a height map are referred to as extracted data points.

The parameter of the recording unit is advantageously detected with a further sensor, wherein the parameter is a speed of the optical recording unit and/or an acceleration of the optical recording unit and/or a spatial position of the optical recording unit and/or a movement of the optical recording unit.

Advantageously, prior to adding a height map to the overall height map, a registration method is selected for the addition as a function of the recording frequency.

BRIEF DESCRIPTION OF THE DRAWINGS

Exemplary embodiments of the invention are shown in the drawing. The following is shown:

FIG. 1 a schematic representation of a first embodiment of a recording method according to the invention.

DETAILED DESCRIPTION OF THE INVENTION

FIG. 1 schematically illustrates a first embodiment of a recording method according to the invention.

According to the exemplary embodiment, a lower jaw 1 with teeth 2 is measured as an object by means of an optical recording unit 3. The optical recording unit 3 is designed as an intraoral camera and comprises a light source 4 and a light detector 6 and is connected to a computing unit 7 with a display means 8.

The measurement is carried out during a time interval T1, wherein the intraoral camera 3 is moved over the teeth 2 of the lower jaw 1 and/or empty spaces in the lower jaw 1. The light source 4 provides an illumination beam 5 and the light detector 6 detects reflected light. The reflected light is detected at a recording frequency $f_A$, wherein a data set is respectively detected by the light detector 6 and transmitted to the computing unit at a time interval $dt=1/f_A$. For each data set, the computing unit respectively calculates a height map $b_i$, i=1 . . . N and stores the latter in a storage medium of the computing unit 8. The recording frequency $f_A$ can be changed so that the time intervals dt between successively recorded height maps $b_i$ are not necessarily identical.

The generated height maps bi are already gradually assembled during the measurement time interval T1 to form an overall height map $b_{ges}$, wherein the overall height map $b_{ges}$ is already displayed by means of the display means 8 during the formation.

It goes without saying that, where applicable, not all generated height maps are used for the overall height map, but that individual height maps are sorted out due to lack of quality, for example. For this purpose, a first height map $b_i$ is stored as an overall height map $b_{ges}$ and displayed. Then, further recorded height maps $b_i$, i=2 . . . N are continuously added to the overall height map $b_{ges}$ and the new overall height map $b_{ges}$ is displayed, wherein a relative alignment of the height map $b_i$ to the overall height map $b_{ges}$ is determined based on an overlap (shown in a hatched fashion) of the height map $b_i$ with the overall height map $b_{ges}$, i.e., the previously recorded height maps $b_i$ in particular the height map $b_{i-1}$ recorded immediately before.

In addition, the recording frequency $f_A$ in the illustrated exemplary embodiment is calculated based on the determined overlap. For the overlap of the last recorded height map $b_i$ with the overall height map $b_{ges}$ a first statistic $M_i$, e.g., the area size of the overlap, is respectively determined and a first control signal $S=S_i(M_i)$ for controlling the recording frequency $f_A$ is generated based on the first statistic Mi. The recording frequency $f_A$ of the light detector 6 is then regulated, i.e., changed where applicable, by means of the control signal S by means of a control unit 10, which is part of the optical recording unit 3 in the illustrated exemplary embodiment. The next height map $b_{i+1}$ is detected accordingly at a time interval $dt_{i+1}=1/f_A$, wherein $f_A$ refers to the regulated recording frequency.

Furthermore, a second statistic for a quality of the height map bi, e.g., an overall intensity or a contrast, is determined based on the last recorded height map bi. A second control signal for controlling the light intensity of the illumination beam 5 is generated based on the second statistic and the light intensity is regulated accordingly or by means of the second control signal. In an alternative embodiment or additionally, a sensor signal of a sensor 9 (shown dashed) is used to calculate the control signal S. For example, the movement of the intraoral camera 3 is tracked by means of an integrated inertial measurement system, wherein the alignment of the individual height maps $b_i$ relative to one another can be deduced from the movement of the camera 4.

LIST OF REFERENCE SIGNS

1 Object
2 Tooth
3 Recording unit
4 Light source
5 Illumination beam
6 Light detector
7 Computing unit
8 Display unit
9 Sensor
10 Control unit
$b_{ges}$ Overall height map
$b_i$ Height maps
$f_A$ Recording frequency
dt Time interval
$M_i$ Statistic
S Control signal
T1 Recording time interval

The invention claimed is:

1. An optical measuring method for the three-dimensional detection of the surface of an object using an optical recording unit, comprising:

moving the optical recording unit relative to the object during a first measurement time interval;

illuminating the object, by the optical recording unit, during the first measurement time interval, using an illumination beam with a light intensity;

successfully detecting, by the optical recording unit, a plurality of height maps each comprising a pixel matrix or image matrix in which each pixel or image point thereof contains three-dimensional information, at a recording frequency during the first measurement time interval;

adding at least a portion of the detected plurality of height maps to an overall height map that represents an accumulation of height maps recorded during the first measurement time interval and displaying the overall height map, wherein the light intensity and/or the recording frequency are regulated during the measurement time interval by means of control signals;

wherein the control signals are generated at time intervals during the measurement time interval, and wherein each control signal is generated on the basis of at least one sensor signal of at least one temperature sensor.

2. The optical measuring method according to claim 1, wherein the control signal is additionally generated on the basis of at least one parameter of the optical recording unit and/or of a last detected height map.

3. Optical measuring method according to claim 2, wherein for generating each control signal for the respectively last detected height map, a statistic of an overlap of the last detected height map with a height map detected immediately before, and/or a statistic of an overlap of the last detected height map with the overall height map is determined and a control signal corresponding to the statistic is then generated.

4. The optical measuring method according to claim 3, wherein the sensor signal of the at least one sensor is taken into account in the determination of the statistic of the overlap.

5. The optical measuring method according to claim 2, wherein, for generating each control signal for the respectively last detected height map, a surface increase of a total surface contained in the overall height map is determined by means of a surface contained in the last detected height map and a control signal corresponding to the surface increase is generated.

6. The optical measuring method according to claim 3, wherein a sampling density or a speed of the optical recording unit is determined from the statistic of the overlap or from the surface increase and is used for generating the control signal.

7. The o-Optical measuring method according to claim 2, wherein, for generating each control signal for the respectively last detected height map, the overall intensity and/or the maximum intensity and/or the contrast and/or the number of extracted data points and/or a quality of extracted data points and/or the signal-to-noise ratio and/or the contrast of an additionally generated color image is determined and used for generating the control signal.

8. The optical measuring method according to claim 2, wherein the parameter of the optical recording unit is detected with another sensor, wherein the parameter is a speed of the optical recording unit and/or an acceleration of the optical recording unit and/or a spatial position of the optical recording unit and/or a movement of the optical recording unit.

9. The optical measuring method according to claim 1, wherein, before adding a height map to the overall height map, a registration method for the addition is selected as a function of the recording frequency.

10. An optical measurement system comprising a processor configured for three-dimensional detection of the surface of an object using an optical recording unit, wherein the processor is further configured to:

illuminate the object, by the optical recording unit, during the first measurement time interval, using an illumination beam with a light intensity;

successfully detect, by the optical recording unit, a plurality of height maps each comprising a pixel matrix or image matrix in which each pixel or image point thereof contains three-dimensional information, at a recording frequency during the first measurement time interval;

add at least a portion of the detected plurality of height maps to an overall height map that represents an accumulation of height maps recorded during the first measurement time interval and display the overall height map, wherein the light intensity and/or the recording frequency are regulated during the measurement time interval by means of control signals;

wherein the control signals are generated at time intervals during the measurement time interval, and wherein each control signal is generated on the basis of at least one sensor signal of at least one temperature sensor.

* * * * *